United States Patent [19]

Schaper et al.

[11] 4,218,388
[45] Aug. 19, 1980

[54] PROCESS FOR PREPARING HYDROCARBONS FROM GASIFICATION OF COAL

[75] Inventors: Lambert Schaper, Amsterdam; Bernardus J. Runderkamp, The Hague; Swan T. Sie, Amsterdam; Nicoline W. Spakman, The Hague, all of Netherlands

[73] Assignee: Shell Oil Company, Houston, Tex.

[21] Appl. No.: 968,324

[22] Filed: Dec. 11, 1978

[30] Foreign Application Priority Data

Dec. 22, 1977 [GB] United Kingdom ............... 53503/77

[51] Int. Cl.² ........................... C07C 3/50; C07C 1/04
[52] U.S. Cl. ................................ 260/449 R; 585/331
[58] Field of Search ......... 260/449 R, 683.48, 449.6R; 585/331

[56] References Cited

U.S. PATENT DOCUMENTS

| 3,972,958 | 8/1976 | Garwood et al. | 260/449 R |
| 4,041,095 | 8/1977 | Kuo | 260/449 R |
| 4,041,096 | 8/1977 | Kuo | 260/683.48 |
| 4,046,830 | 9/1977 | Kuo | 585/331 |
| 4,086,262 | 4/1978 | Chang et al. | 260/449 R |
| 4,096,163 | 6/1978 | Chang et al. | 260/449 R |

OTHER PUBLICATIONS

Elliott, M. *Gas Manufactured* in Encyclopedia of Chemical Technology, ed. by Kirk-Othmer, 2nd Ed. vol. X pp. 353-387.

*Primary Examiner*—George Crasanakis

[57] ABSTRACT

Synthesis gas is converted into gasoline by contacting the gas with a crystalline aluminosilicate zeolite catalyst, the process being characterized by conversion of by-product isobutane into gasoline by alkylation.

1 Claim, 1 Drawing Figure

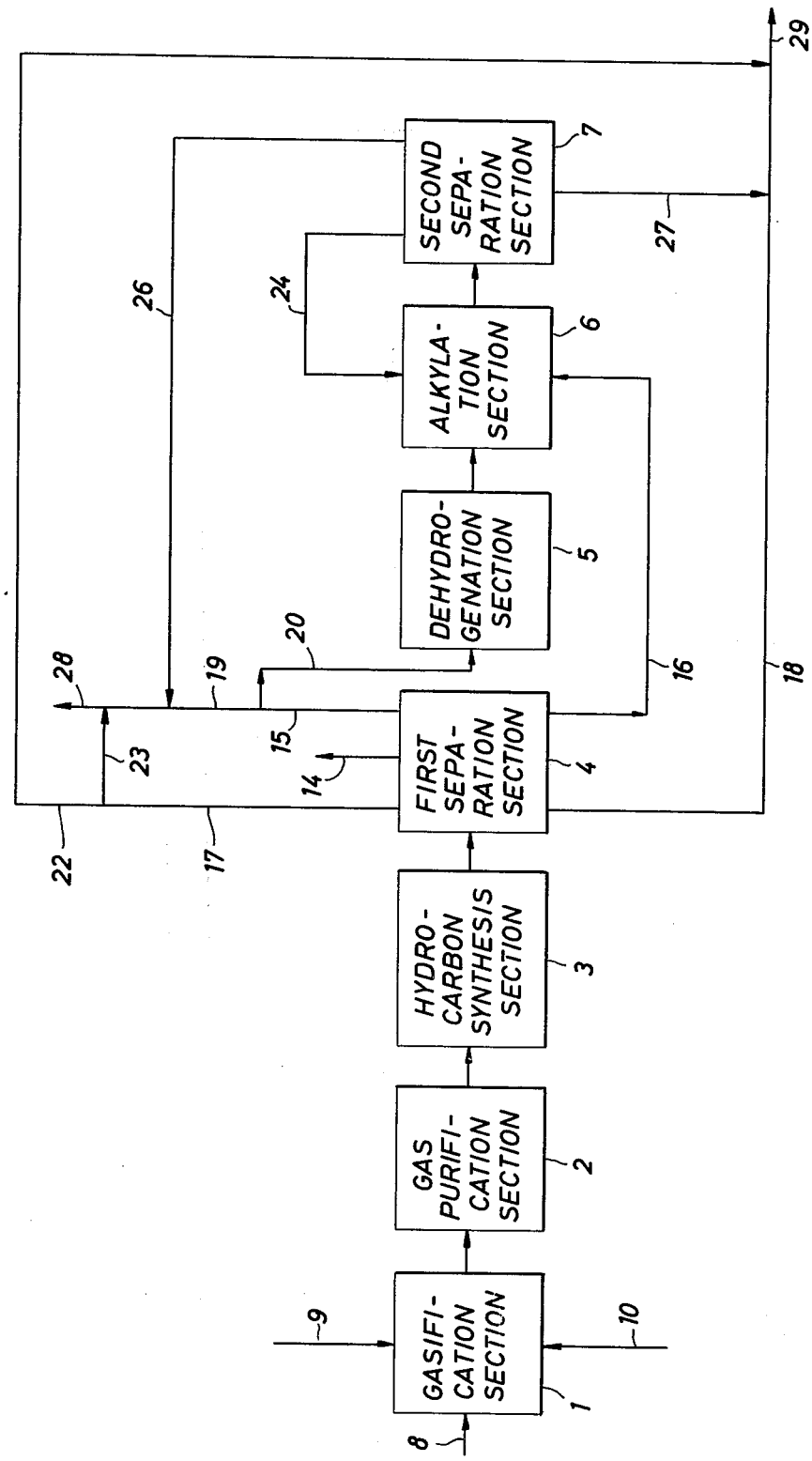

PROCESS FOR PREPARING HYDROCARBONS FROM GASIFICATION OF COAL

BACKGROUND OF THE INVENTION

The invention relates to a process for preparing liquid hydrocarbons from coal.

Hydrocarbon mixtures boiling in the gasoline range can be obtained, for instance, by straight-run distillation of crude mineral oil, by conversion of heavy mineral oil fractions, for instance, by catalytic cracking, thermal cracking and hydrocracking, and by conversion of light mineral oil fractions, for instance by alkylation.

In view of the increasing need of gasoline and the decreasing reserves of mineral oil there is a great interest in processes having the potentialities of converting carbon-containing materials not based on mineral oil, such as coal, in an economically justified way into hydrocarbon mixtures boiling in the gasoline range.

It is known that carbon-containing materials, such as coal, can be converted into mixtures of carbon monoxide and hydrogen by gasification. It is further known that mixtures of carbon monoxide and hydrogen can be converted into mixtures of hydrocarbons by contacting the gas mixtures with suitable catalysts. Finally, it is known that mixtures of paraffins and olefins boiling below the gasoline range can be converted into hydrocarbon mixtures boiling in the gasoline range by contacting the mixtures first mentioned with an alkylation catalyst.

Investigation has shown that gasoline having a high octane number can be prepared from coal by combining the three above-mentioned processes, provided that the following conditions are satisfied.

First of all, the gasification of the coal should be carried out at a temperature of from 1050° to 2000° C. From the mixture of carbon monoxide and hydrogen thus obtained an aromatic hydrocarbon mixture should then be prepared using a catalyst which contains a crystalline aluminosilicate zeolite having an $SiO_2/Al_2O_3$ molar ratio of at least 12 and a constraint index between 1 and 12. From the aromatic hydrocarbon mixture thus obtained two fractions should then be separated, viz. an isobutane-containing gaseous fraction, which is contacted with an alkylation catalyst and an aromatic liquid fraction boiling in the gasoline range. Finally, a fraction boiling in the gasoline range is separated from the product obtained in the alkylation, and this fraction is mixed with the gasoline fraction that was separated from the reaction product of carbon monoxide and hydrogen.

SUMMARY OF THE INVENTION

The present invention, therefore, relates to a process for preparing liquid hydrocarbons from coal, in which (a) the coal is converted into a mixture of carbon monoxide and hydrogen by gasification at a temperature between 1050° and 2000° C.;

(b) the mixture of carbon monoxide and hydrogen is converted into an aromatic hydrocarbon mixture using a catalyst which contains a crystalline aluminosilicate zeolite having an $SiO_2/Al_2O_3$ molar ratio of at least 12 and a constraint index between 1 and 12;

(c) from the aromatic hydrocarbon mixture an isobutane-containing gaseous fraction and an aromatic liquid fraction boiling in the gasoline range are separated;

(d) the isobutane-containing gaseous fraction is converted by alkylation into a product from which a fraction boiling in the gasoline range is separated, and (e) the two fractions boiling in the gasoline range obtained according to (c) and (d) are mixed.

In the first step of the process according to the invention, a mixture of carbon monoxide and hydrogen is prepared by gasification of coal at a temperature between 1050° and 2000° C. As a result of the use of this high temperature, the synthesis gas prepared contains very little methane, if any at all. In comparison with a process in which in the first step a lower temperature is used, for instance between 800° and 1000° C., the process according to the invention gives a higher yield of CO and $H_2$ per ton of coal and a higher gasoline yield per ton of coal. Because of the use of a gasification temperature between 1050° and 2000° C. the product contains very small amounts of non-gaseous by-products such as tar, phenols and condensable hydrocarbons, if any at all. The absence of these products also leads to a higher yield of CO and $H_2$, and therefore to a higher gasoline yield than when a lower temperature is used in the gasification step. In addition, no provisions have to be made to remove tar, phenols and condensable hydrocarbons from the synthesis gas, which will promote the economy of the gasoline preparation.

The starting materials in the process according to the invention may, for instance, be: lignite, bituminous coal, subbituminous coal, anthracite and coke. With a view to achieving more rapid and complete gasification, it is preferred first to reduce the starting material to powder. The high-temperature gasification is preferably carried out in the presence of oxygen and steam. It is preferred to choose such an oxygen/steam ratio that per part by volume of oxygen from 5 to 150%v steam is present. The oxygen used is preferably preheated before it is contacted with the coal. This preheating can very conveniently be carried out by heat exchange, for instance, with the hot product gas prepared according to step (a) of the process. By preheating, the oxygen is preferably brought to a temperature between 200° and 500° C. The reactor in which the gasification is carried out preferably consists of an empty steel vessel lined with a heat-resistant material. A suitable reactor is described in British patent applications Nos. 18550/75 and 35133/75. The high temperature at which the gasification is effected is produced by the reaction of the coal with oxygen and steam. The mixture to be reacted is preferably introduced into the reactor at high speed. A suitable linear speed is 10 to 100 m/s. The pressure at which the gasification is carried out may vary within wide limits. The absolute pressure is preferably 1 to 200 bar. In order to convert as much as possible of the coal introduced into the reactor into gas, the coal particles should remain in the reactor for some time. It has been found that a residence time of from 0.1 to 12 seconds is sufficient for this purpose. After the coal has been converted into gas, the reaction product, which consists substantially of $H_2$, CO, $CO_2$ and $H_2O$, is removed from the reactor. This gas, which has as a rule a temperature higher than 1100° C., may contain impurities such as ash, carbon-containing solids and hydrogen sulphide. To allow the impurities to be removed from the gas, the latter should first be cooled. This cooling can very suitably be effected in a boiler, in which steam is formed with the aid of the waste heat. Although as a rule the solids content of the crude gas that leaves the boiler is low, a further reduction of the solids content may nevertheless be desirable, for instance, if the gas is to be desulphurized. To this end the gas is preferably conducted through a scrubber where it is washed with water. An apparatus for this purpose is described in British Pat. No. 826,209. Such a washing produces a gas containing hardly any solids any more and having a temperature between 20° and 80° C. The gas may be purified still further by removal of $H_2S$ and, if desired, part of the $CO_2$. The removal of $H_2S$ and $CO_2$ is preferably carried out with the aid of the absorption processes, such as those processes described in British Pat. Nos. 1,444,963, 1,131,989, 965,358, 957,260 and 972,140.

The mixture of carbon monoxide and hydrogen prepared according to the first step of the process according to the invention is converted in the second step into an aromatic hydrocarbon mixture using a catalyst which contains a crystalline aluminosilicate zeolite of a special class. These zeolites effect a high conversion of aliphatic hydrocarbons into aromatic hydrocarbons in commercially desirable yields and they are in general very active in conversion reactions in which aromatic hydrocarbons are involved. Although they have an uncommonly low alumina content, i.e. a high $SiO_2/Al_2O_3$ molar ratio, they are very active, even when the $SiO_2/Al_2O_3$ molar ratio is more than 30. This activity is surprising, because the catalytic activity of zeolites is generally ascribed to the aluminum atoms of the lattice and the cations present in combination with these aluminum atoms. These zeolites retain their crystalline character for a very long time in spite of the presence of steam, even at high temperatures such as those which effect irreversible collapse of the crystal lattice of other zeolites, e.g. those of the X- and A-type. If carbon-containing deposits are formed, they can be removed by burning them at temperatures that are higher than the temperatures usually employed for restoring the activity. In many media zeolites of this group show a very slight capability of forming coke, as a result of which the operational times between regenerations are very long.

An important property of the crystal structure of this class of zeolites is that it provides constrained access to and egress from the intracrystalline free space, because the pore size is more than about 5 Å and the pore windows are of about the same size as are provided by rings of 10 oxygen atoms. Obviously, these rings are those formed by the regular arrangement of the tetrahedrons forming the anionogenic lattice of the crystalline aluminosilicate, the oxygen atoms themselves being bound to the silicon or aluminum atoms in the centers of the tetrahydrons. In short, the zeolites that are preferably used according to the invention have a ratio of silica to alumina of at least 12 and a structure that gives constrained access to the free space in the crystals.

The said ratio of silica to alumina can be determined by usual analysis. This ratio serves the purpose of representing as precisely as possible the ratio in the rigid anionogenic lattice of the zeolite crystal, so that aluminum in the binder material or in cationogenic or other form in the channels is excluded. Although zeolites having a molar $SiO_2/Al_2O_3$ ratio of at least 12 are suitable, use is preferably made of zeolites having a higher ratio of at least 30 and in particular having an $SiO_2/Al_2O_3$ ratio between 60 and 400. After activation, these zeolites obtain an intracrystalline sorptive power for n-hexane that is greater than for water, i.e. they show hydrophobic properties. It is assumed that this hydrophobic nature is an advantage in the present invention.

The zeolites that are suitable according to the invention freely sorb n-hexane and have a pore size of more than 5 Å. The structure must further provide constrained access to certain large molecules. Sometimes it is possible to infer from a known crystal structure whether such a constrained access exists. If, for instance, the only pore windows in a crystal are formed by rings of eight oxygen atoms, the access for molecules having a larger cross-section than n-hexane is excluded and then the zeolite is not of the desired type. Zeolites with windows of rings with 10 atoms are preferred, although an excessive puckering or pore blockage may deactivate these zeolites. In general, zeolites with windows of rings with 12 atoms have been found to give no sufficiently constrained access to effect the conversions desired according to the invention, although as a result of pore blockage or other causes structures are possible here which are active.

Instead of trying to judge from the crystal structure whether a zeolite has the required constrained access or not, a simple constraint index determination can be carried out by continuously passing a mixture of equal quantities by weight of n-hexane and 3-methylpentane at atmospheric pressure over a small sample, about 1 g or less, of the zeolite according to the process given hereinafter. A sample of the zeolite in the form of granules or extrudate is ground to a particle size which is about equal to that of coarse sand and introduced into a glass tube. Before the examination the zeolite is treated for at least 15 minutes with a stream of air of about 538° C. The zeolite is thereupon purged with helium and the temperature is set at a value between about 285° C. and about 510° C. to give a total conversion between 10% and 60%. The mixture of hydrocarbons is passed over the zeolite at a volume velocity of 1 (i.e. 1 volume of liquid hydrocarbon per volume of zeolite per hour), the mixture being diluted with helium such that the molar ratio of helium to total hydrocarbons is 4:1. After a running time of 20 minutes a sample of the effluent is taken and analysed (the best way is gas chromatography) in order to determine the fraction of each of the two hydrocarbons that has not been converted.

The constraint index is calculated as follows:

$$\text{constraint index} = \frac{^{10}\!\log \text{ (remaining fraction of n-hexane)}}{^{10}\!\log \text{ (remaining fraction of 3-methylpentane)}}$$

The constraint index approaches the ratio of the velocity constants for cracking the two hydrocarbons. Catalysts which are suitable for the present process are those containing a zeolite with a constraint index between 1 to 12. For some representative materials, some of which fall outside the scope of the invention, the values for the constraint index (CI) are given below:

|  | CI |
|---|---|
| ZSM-5 | 8.3 |
| ZSM-11 | 8.7 |
| ZSM-12 | 2 |
| ZSM-38 | 2 |
| ZSM-35 | 4.5 |
| TMA-offretite | 3.7 |
| Beta | 0.6 |
| ZSM-4 | 0.5 |
| Acid mordenite | 0.5 |
| REY | 0.4 |

| | CI |
|---|---|
| Amorphorous silica-alumina | 0.6 |
| Erionite | 38 |

Examples of zeolites of the class defined here are ZSM-5, ZSM-11, ZSM-12, ZSM-35 and ZSM-38. U.S. Pat. No. 3,702,886 describes ZSM-5. ZSM-11 is described in U.S. Pat. No. 3,709,979 and ZSM-12 in U.S. Pat. No. 3,832,449. U.S. patent applications Nos. 528,061 and 528,060 describe ZSM-35 and ZSM-38, respectively.

Naturally occurring zeolites may sometimes be converted into this type of zeolite by various activation methods and other treatments such as base exchange, steam treatment, alumina extraction and calcination or combinations of these treatments. Of the naturally occurring minerals that may be treated in this way are to be mentioned: ferrierite, brewsterite, stilbite, dachiardite, epistilbite, heulandite and clinoptilolite. The crystalline aluminosilicate zeolites which are preferably used are ZSM-5, ZSM-11, ZSM-12, ZSM-35 and ZSM-38, particular preference being given to ZSM-5.

According to a preferred aspect of the invention the zeolites used in the catalysts have in the dry hydrogen form a crystal lattice density of at least 1.6 g per cm$^3$. The dry-state density can for known structures be calculated from the number of silicon plus aluminum atoms per 1000 Å$^3$, as described for instance on page 19 of the article on zeolite structure by W. U. Meier. This article is to be found in "Proceedings of the Conference on Molecular Sieves", London, April 1967, published by the Society of Chemical Industry, London, 1968. If the crystal structure is unknown, the density of the crystal lattice can be determined according to classical pycnometer methods. The density may be determined, for instance, by immersing the zeolite in the dry hydrogen form in an organic solvent which is not sorbed by the crystal. It may be that the extraordinary, long lasting activity and stability of this class of zeolites is connected with the high density of the anionogenic lattice of the crystal, which is at least 1.6 g per cm$^3$. Obviously, this high density has to be associated with a relatively small free space in the crystal, which may be expected to lead to stabler structures. However, this free space seems to be important as the seat of the catalytic activity.

Below the densities are given of the crystal lattice of some representative zeolites, of which some fall outside the scope of the invention.

| Zeolite | Volume of cavities, cm$^3$/cm$^3$ | Density of lattice, g/cm$^3$ |
|---|---|---|
| Ferrierite | 0.28 | 1.76 |
| Mordenite | 0.28 | 1.7 |
| ZSM-5, -11 | 0.29 | 1.79 |
| Dachiardite | 0.32 | 1.72 |
| L | 0.32 | 1.61 |
| Clinoptilolite | 0.34 | 1.71 |
| Laumontite | 0.34 | 1.77 |
| ZSM-4 (omega) | 0.38 | 1.65 |
| Heulandite | 0.39 | 1.69 |
| P | 0.41 | 1.57 |
| Offretite | 0.40 | 1.55 |
| Levynite | 0.40 | 1.54 |
| Erionite | 0.35 | 1.51 |
| Gmelenite | 0.44 | 1.46 |
| Chabazite | 0.47 | 1.45 |
| A | 0.5 | 1.3 |
| Y | 0.48 | 1.27 |

In step (b) of the process according to the invention a mixture of carbon monoxide and hydrogen should be converted into an aromatic hydrocarbon mixture. Step (b) may in itself be carried out as a one-step or as a two-step process. In the two-step process the mixture of carbon monoxide and hydrogen is contacted in the first step with a catalyst containing one or more metal components having catalytic activity for the conversion of a H$_2$/CO mixture into hydrocarbons and/or oxygen-containing hydrocarbons. In the second step the product thus obtained is converted into an aromatic hydrocarbon mixture by contacting it under aromatization conditions with the crystalline aluminosilicate zeolite. In the one-step process the mixture of carbon monoxide and hydrogen is contacted with a bifunctional catalyst which contains, in addition to the crystalline aluminosilicate zeolite, one or more metal compounds having catalytic activity for the conversion of a H$_2$/CO mixture into hydrocarbons and/or oxygen-containing hydrocarbons. Step (b) of the process according to the invention is preferably carried out as a one-step process.

According to step (a) in the process according to the invention a H$_2$/CO mixture is prepared, whose H$_2$/CO molar ratio, depending on starting material and reaction conditions, may vary within wide limits. Before this mixture is further converted according to step (b) its H$_2$/CO molar ratio can be changed by adding hydrogen or carbon monoxide. The hydrogen content of the mixture may also be increased by subjecting it to the known water gas shift reaction.

As the feed for step (b) of the process according to the invention use is preferably made of a gas mixture whose H$_2$/CO molar ratio is more than 0.4. If the mixture of carbon monoxide and hydrogen used in the process according to the invention as the feed for step (b) has a H$_2$/CO molar ratio of less than 1.0, step (b) is preferably carried out as a one-step process by contacting the gas with a trifunctional catalyst which contains one or more metal components having catalytic activity for the conversion of a H$_2$/CO mixture into hydrocarbons and/or oxygen-containing hydrocarbons, one or more metal components having catalytic activity for the water gas shift reaction and the crystalline aluminosilicate zeolite. The ratio in which the three catalytic functions are present in the catalyst may vary within wide limits and is chiefly determined by the activity of each of the catalytic functions. When use is made of a trifunctional catalyst in step (b) of the process according to the invention for converting a H$_2$/CO mixture with a H$_2$/CO molar ratio of less than 1.0, the object is that of the acyclic hydrocarbons and/or oxygen-containing hydrocarbons formed under the influence of a first catalytic function, as much as possible is converted under the influence of a second catalytic function into an aromatic hydrocarbon mixture substantially boiling in the gasoline range, and that of the water liberated in the conversion of the mixture of carbon monoxide and hydrogen into hydrocarbons and/or in the conversion of oxygen-containing hydrocarbons into an aromatic hydrocarbon mixture, as much as possible reacts under the influence of a third catalytic function with the carbon monoxide present in an excess amount in the mixture of carbon monoxide and hydrogen with formation of a mixture of hydrogen and carbon dioxide. In the composition of an optimum trifunctional catalyst to be used in step (b) of the process according to the invention, which catalyst contains a given quantity of a first catalytic function having a given activity, it is therefore possible to do with less of the other catalytic functions according as these are more active.

Although the trifunctional catalysts that can be used in step (b) of the process according to the invention are described in this patent application as catalysts containing one or more metal components having catalytic activity for the conversion of a $H_2/CO$ mixture into hydrocarbons and one or more metal components having catalytic activity for the water gas shift reaction, this means in no way that metal components each having in themselves one of the two catalytic functions should always separately be present in the catalysts. For, it has been found that metal components and combinations of metal components having catalytic activity for the conversion of a $H_2/CO$ mixture into substantially oxygen-containing hydrocarbons as a rule also have sufficient catalytic activity for the water gas shift reaction, so that in such a case incorporation of one metal component or one combination of metal components into the catalysts will suffice. Examples of such metal components are the metals chosen from the group formed by the metals zinc, copper and chromium. When use is made of trifunctional catalysts containing these metals in step (b) of the process according to the invention, preference is given to catalysts containing combinations of at least two of these metals, for instance the combination zinc-copper, zinc-chromium or zinc-copper-chromium. Particular preference is given to a trifunctional catalyst containing in addition to the crystalline aluminosilicate zeolite the metal combination zinc-chromium. Metal components and combinations of metal components having catalytic activity for the conversion of a $H_2/CO$ mixture into substantially hydrocarbons have as a rule no or insufficient activity for the water gas shift reaction. When use is made of such metal components or combinations of metal components in the catalysts, one or more separate metal components having catalytic activity for the water gas shift reaction should therefore be incorporated therein.

The trifunctional catalysts which are used in step (b) of the process according to the invention are preferably composed of two or three separated catalysts, which will for convenience be designated catalysts X, Y and Z. Catalyst X is the catalyst containing the metal components having catalytic activity for the conversion of a $H_2/CO$ mixture into hydrocarbons and/or oxygen-containing hydrocarbons. Catalyst Y is the crystalline aluminosilicate zeolite. Catalyst Z is the catalyst containing the metal component having catalytic activity for the water gas shift reaction. As has been explained hereinbefore the use of a Z-catalyst may be omitted in some cases.

If as the X-catalyst a catalyst is used which is capable of converting a $H_2/CO$ mixture into substantially oxygen-containing hydrocarbons, preference is given to a catalyst which is capable of converting the $H_2/CO$ mixture into substantially methanol and/or dimethyl ether. For the conversion of a $H_2/CO$ mixture into substantially methanol, catalysts containing the metal combinations mentioned hereinbefore are very suitable. If desired, the said metal combinations may be emplaced on a carrier material. By introducing an acid function into these catalysts, for instance by emplacing the metal combination on an acid carrier, it may be effected that apart from the conversion of the $H_2/CO$ mixture into methanol a considerable part of the mixture will be converted into dimethyl ether.

X-catalysts which are capable of converting a $H_2/CO$ mixture into substantially hydrocarbons are referred to in the literature as Fischer-Tropsch catalysts. Such catalysts often contain one or more metals of the iron group or ruthenium together with one or more promoters to increase the activity and/or selectivity and sometimes a carrier material such as kieselguhr. They can be prepared by precipitation, melting and by impregnation. The preparation of the catalysts containing one or more metals of the iron group, by impregnation, takes place by impregnating a porous carrier with one or more aqueous solutions of salts of metals of the iron group and, optionally, of promoters, followed by drying and calcining the composition. If in step (b) of the process according to the invention use is made of a catalyst combination in which catalyst X is a Fischer-Tropsch catalyst, it is preferred to choose for this purpose an iron or cobalt catalyst, in particular such a catalyst which has been prepared by impregnation. Very suitable Fischer-Tropsch catalysts for use in the catalyst combinations according to the invention are the catalysts prepared by impregnation according to the Netherlands patent application No. 7612.460. The catalysts concerned contain per 100 pbw carrier 10–75 pbw of one or more metals of the iron group, together with one or more promoters in a quantity of 1–50% of the quantity of metals of the iron group present on the catalyst, which catalysts have such a specific average pore diameter (p) of at most 10.000 nm and such a specific average particle diameter (d) of at most 5 mm, that the quotient p/d is more than 2 (p in nm and d in mm).

If in step (b) of the process according to the invention the object is to use a catalyst combination of which X is a Fischer-Tropsch iron catalyst, it is preferred to choose an iron catalyst containig a promoter combination consisting of an alkali metal, a metal that is easy to reduce, such as copper or silver and, optionally, a metal that is hard to reduce, such as aluminum or zinc. A very suitable iron catalyst for the present purpose is a catalyst prepared by impregnation containing iron, potassium and copper on silica as the carrier. If in step (b) of the process according to the invention the object is to use a catalyst combination of which X is a Fischer-Tropsch cobalt catalyst, it is preferred to choose a cobalt catalyst containing a promoter combination consisting of an alkaline-earth metal and thorium, uranium or cerium. A very suitable Fischer-Tropsch cobalt catalyst for the present purpose is a catalyst prepared by impregnation containing cobalt, magnesium and thorium on silica as the carrier. Other very suitable Fischer-Tropsch cobalt catalysts prepared by impregnation are catalysts containing, in addition to cobalt, one of the elements chromium, titanium, zirconium and zinc on silica as the carrier. If desired, it is also possible to use in step (b) of the process according to the invention catalyst combinations containing an X-catalyst, which is capable of converting a $H_2/CO$ mixture into a mixture containing both hydrocarbons and oxygen-containing hydrocarbons in comparable quantities. As a rule, such a catalyst has sufficient catalytic activity for the water gas shift reaction, so that the use of a Z-catalyst in the combination can be omitted. An example of an X-catalyst of this type is an iron-chromium oxide catalyst.

If desired, it is also possible to use in step (b) of the process according to the invention catalyst combinations containing two or more X-catalysts, for instance in addition to a catalyst of the X-type which is capable of converting a $H_2/CO$ mixture into substantially hydrocarbons, a second catalyst of the X-type which is capable of converting a $H_2/CO$ mixture into substantially oxygen-containing hydrocarbons.

Z-catalysts which are capable of converting a $H_2O/CO$ mixture into a $H_2/CO_2$ mixture are referred to in the literature as CO-shift catalysts. Such catalysts often contain one or more metals of the group formed by iron, chromium, copper, zinc, cobalt, nickel and molybdenum as the catalytically active component, either as such, or in the form of their oxides or sulphides. Examples of suitable CO-shift catalysts are the mixed sulphidic catalysts according to the Netherlands patent applications No. 7305340 and No. 7304793 and the spinel catalysts according to the French patent application No. 7633900. If in step (b) of the process according to the invention use is made of a catalyst combination in which a Z-catalyst is present, it is preferred to choose a catalyst which contains both copper and zinc, in particular a catalyst in which the Cu/Zn atom ratio lies between 0.25 and 4.0.

In the trifunctional catalysts the catalysts X, Y and, optionally, Z may be present as a mixture, in which in principle, each particle of catalyst X is surrounded by a number of particles of catalyst Y and, optionally, catalyst Z and conversely. If the process is carried out with use of a fixed catalyst bed, this bed may be built up of alternate layers of particles of catalysts X, Y and, optionally, Z. If the two or three catalysts are used as a mixture, this mixture may be a macromixture or a micromixture. In the first case the trifunctional catalyst consists of two or three kinds of macroparticles of which one kind is completely made up of catalyst X, the second kind completely of catalyst Y and, optionally, a third kind completely of catalyst Z. In the second case the trifunctional catalyst consists of one kind of macroparticles, each macroparticle being made up of a large number of microparticles of each of the catalysts X, Y and, optionally, Z. Trifunctional catalysts in the form of micromixtures may be prepared, for instance, by thoroughly mixing a fine powder of catalyst X with a fine powder of catalyst Y and, optionally, with a fine powder of catalyst Z and shaping the mixture to larger particles, for instance, by extruding or pelletizing. In step (b) of the process according to the invention it is preferred to use trifunctional catalysts in the form of micromixtures. The trifunctional catalysts may also have been prepared by incorporating the metal components having catalytic activity for converting a $H_2/CO$ mixture into hydrocarbons and/or oxygen-containing hydrocarbons and, optionally, the metal components having catalytic activity for the water gas shift reaction into the crystalline aluminosilicate zeolite, for instance by impregnation or by ion exchange.

The crystalline aluminosilicate zeolites which are used in step (b) of the process according to the invention are usually prepared from an aqueous mixture as the starting material which contains the following compounds in a given ratio: one or more compounds of an alkali or alkaline-earth metal, one or more compounds containing a mono- or bivalent organic cation or from which such a cation is formed during the preparation of the zeolite, one or more silicon compounds and one or more aluminum compounds. The preparation is effected by maintaining the mixture at elevated temperature until the zeolite has been formed and then separating the crystals of the zeolite from the mother liquor. The zeolites thus prepared contain alkali and/or alkaline-earth metal ions and mono- and/or bivalent organic cations. Before being used in step (b) of the process according to the invention at least part of the mono- and/or bivalent organic cations introduced during the preparation are preferably converted into hydrogen ions, for instance by calcining and at least part of the exchangeable mono- and/or bivalent cations introduced during the preparation are preferably replaced by other ions, in particular hydrogen ions, ammonium ions and/or ions of the rare-earth metals. The crystalline aluminosilicate zeolites used in step (b) of the process according to the invention preferably have an alkali metal content of less than 1%w and in particular of less than 0.05%w. If desired, a binder material such as bentonite or kaolin may be incorporated into the catalysts that are used in step (b) of the process according to the invention.

Step (b) of the process according to the invention is preferably carried out at a temperature of from 200° to 500° C. and in particular of from 300° to 450° C., a pressure of from 1 to 150 bar and in particular of from 5 to 100 bar and a space velocity of from 50 to 5000 and in particular of from 300 to 3000 Nl gas/l catalyst/hour.

Step (b) of the process according to the invention can very suitably be carried out by passing the feed in upward or in downward direction through a vertically disposed reactor in which a fixed or a moving bed of the trifunctional catalyst concerned is present. Step (b) of the process may, for instance, be carried out in the so-called fixed-bed operation, in bunker-flow operation or in ebulated-bed operation. It is preferred to use catalyst particles then with a diameter between 1 and 5 mm. If desired, step (b) of the process may also be carried out in fluidized-bed operation or with the use of a suspension of the catalyst in a hydrocarbon oil. It is preferred to use catalyst particles then with a diameter between 10 and 150 mm.

In the process according to the invention an isobutane-containing gaseous fraction and an aromatic liquid fraction boiling in the gasoline range should be separated from aromatic hydrocarbon mixture obtained according to step (b). It is preferred to separate the reaction mixture originating from step (b) in step (c) into a $C_2^-$ fraction, a propane fraction, an isobutane-containing fraction, an n-butane fraction and an aromatic liquid fraction boiling in the gasoline range. The $C_2^-$ fraction may be used as fuel gas. If desired, a $H_2/CO$ mixture can be separated from the $C_2^-$ fraction, which mixture may be recirculated to step (b).

In step (d) of the process according to the invention the isobutane-containing gaseous fraction should be converted by alkylation into a product from which a fraction boiling in the gasoline range can be separated. This alkylation can very conveniently be effected by contacting the fraction with a strong acid as the catalyst, such as sulphuric acid or hydrofluoric acid. Since the gaseous part of the reaction product of step (b) usually contains only small amounts of olefins, the isobutane-containing gaseous fraction which is separated from it will often have too low an olefin content to realize a sufficient conversion of the isobutane present in it by alkylation. It is therefore preferred to increase the olefin content of the fraction before subjecting it to alkylation. An increase in the olefin content of the isobutane-containing fraction can conveniently be effected by mixing it with an olefin-rich stream which may originate from an external source or which has been prepared by dehydrogenation of the paraffins obtained in the process, such as a propane fraction, an n-butane-fraction or an LPG fraction obtained from it by mixing. Dehydrogenation of these fractions can conveniently be effected by contacting them at elevated temperature with a chromium-containing catalyst. From the product obtained in the alkylation a fraction boiling in the gasoline range is separated and this fraction is mixed according to step (e) of the process according to the invention with the aromatic liquid fraction obtained in step (c) and boiling in the gasoline range. The non-converted isobutane is preferably separated from the product obtained in the alkylation and recirculated to the alkylation reaction. In order to increase the vapor pressure of the gasoline mixture thus obtained, light hydrocarbons are preferably added to it. As light hydrocarbons use can very conveniently be made of n-butane or LPG, which may be obtained as by-products of the process.

In order to illustrate the invention more fully, reference is made to the accompanying drawing.

In accordance with a preferred aspect of the invention, the process is carried out in an apparatus comprising succesively a gasification section (1), a gas purification section (2), a hydrocarbon synthesis section (3), the first separation section (4) a dehydrogenation section (5), an alkylation section (6) and the second separation section (7). A mixture of coal (8), oxygen (9) and steam (10) is gasified, the crude gas (11) is purified and the purified gas (12) is converted under the influence of trifunctional catalyst according to the invention into an aromatic hydrocarbon mixture (13). This hydrocarbon mixture is separated into a $C_2^-$ fraction (14), a propane fraction (15), an isobutane fraction (16) an n-butane fraction (17) and an aromatic gasoline fraction (18). The propane fraction (15) is separated into two portions (19) and (20). Portion (20) is converted by dehydrogenation into a mixture of propene and propane (21). The n-butane fraction (17) is separated into two portions (22) and (23). The isobutane fraction (16) is alkylated together with the propane/propene stream (21) and with an isobutane recirculation stream (24) reverted to later. From the alkylated product (25) a propane fraction (26), the isobutane recirculation stream (24) and a gasoline fraction (27) are separated. The propane fraction (26) is mixed with portion (19) of the propane fraction (15) and with portion (23) of the n-butane fraction (17) into the LPG fraction (28). The gasoline fraction (27) is mixed with the gasoline fraction (18) and with portion (22) of n-butane fraction (17) into the gasoline (29).

The invention will now be further explained with the aid of the following examples.

EXAMPLE I

ZSM-5 (zeolite A) was prepared as follows: A mixture of $SiO_2$, $NaAlO_2$, $NaOH$ and $[(C_3H_7)_4N]OH$ in water with the molar composition 1.21 $Na_2O$. $Al_2O_3$. 9$[(C_3H_7)_4N]_2O$. 29.1 $SiO_2$. 480 $H_2O$ was heated for 98 hours in an autoclave at 150° C. under autogenous pressure. After having cooled the reaction mixture, the zeolite formed was filtered off, washed with water until the pH of the wash water was about 8 and dried for two hours at 120° C. With zeolite A as the starting material zeolite B was prepared by, successively, calcining zeolite A at 500° C., boiling with 1.0 molar $NH_4NO_3$ solution, washing with water, boiling again with 1.0 molar $NH_4NO_3$ solution and washing, drying for two hours at 120° C. and calcining for four hours at 500° C.

EXAMPLE II

A catalyst C was prepared by mixing a $ZnO-Cr_2O_3$ composition with zeolite B in a weight ratio of 5:1. Both materials were present in the catalyst in the form of particles having a diameter of 0.15–0.3 mm. The $ZnO-Cr_2O_3$ composition used catalyses both the reduction of CO to methanol and the water gas shift reaction.

EXAMPLE III

Bituminous coal was ground to a particle size of less than 120 microns and used as the feed for a high-temperature coal gasifier. Per gram of coal 0.9 g oxygen and 0.15 g steam were added. The coal gasification was effected at a temperature of 1500° C., a pressure of 30 bar and a residence time of 0.5 s. The coal conversion was 99%. The gas obtained had the following composition:

|  | % v |
| --- | --- |
| $CH_4$ | 0.1 |
| CO | 64.7 |
| $H_2$ | 31.8 |
| $CO_2$ | 1.7 |

The gas further contained about 1.7%v $H_2O$, COS and $H_2S$. To remove the last-mentioned impurities from the gas, this gas was passed at about 45° C. through a mixture of diisopropyl amine, sulfolane and water. The resulting synthesis gas, of which the $CO/H_2$ molar ratio was 2.03, was further purified by passing it at 200° C. over ZnO. The synthesis gas thus purified was used in Example IV which was carried out according to the process scheme described, supra.

EXAMPLE IV

The synthesis gas prepared according to Example III was contacted at a temperature of 375° C., a pressure of 60 bar and a space velocity of 300 $1.1^{-1}.h^{-1}$ with catalyst c. The synthesis gas conversion was 95%. The reaction developed completely to carbon dioxide. The hydrocarbon mixture obtained had the following composition:

|  | % w |
| --- | --- |
| $C_1$ | 4 |
| $C_2$ | 6 |
| $C_3$ | 39 |
| $n-C_4$ | 3 |
| $i-C_4$ | 8 |
| $C_5^+$ gasoline | 42 |

The olefin content of both the $C_3$ and the $C_4$ fractions was less than 1%w. The reaction product was separated by cooling into a $C_2^-$ fraction (including carbon dioxide and unconverted synthesis gas) and a $C_3^+$ fraction. The $C_3^+$ fraction was separated into a propane fraction, an isobutane fraction, an n-butane fraction and a $C_5^+$ gasoline fraction mainly consisting of aromatics. The propane fraction was divided into two equal portions of which one was converted by dehydrogenation at 600° C. over a $Cr_2O_3$ catalyst into a mixture of propane and propene. The conversion from propane into propene was 30%. The propane/propene mixture thus obtained was mixed with the isobutane fraction and the mixture was converted by contacting it at 40° C. with a HF alkylation catalyst. From the product obtained in the alkylation a propane fraction an isobutane fraction and a gasoline fraction were separated. By recirculation of isobutane a constant isobutane/olefin ratio of 14 was maintained. The alkylation gasoline yield was 94%. The alkylation gasoline was mixed with the gasoline obtained earlier in the process. To bring the vapor pressure of the mixture to the proper value, part of the n-butane fraction was added. The gasoline thus obtained had an octane number (CRON) of 96. The remaining part of both the propane fraction and the n-butane fraction obtained from the $C_3^+$ fraction of the hydrocarbon synthesis product were mixed with the propane fraction obtained from the alkylation product, into LPG.

What is claimed is:

1. A process for preparing liquid hydrocarbons from coal, comprising:

(a) converting coal into a mixture of carbon monoxide and hydrogen by gasification at a temperature between 1050° C. and 2000° C.;

(b) converting the mixture of carbon monoxide and hydrogen into an aromatic hydrocarbon mixture in the presence of a catalyst which contains a crystalline aluminosilicate zeolite having an $SiO_2/Al_2O_3$ molar ratio of at least 12 and a constraint index between 1 and 12;

(c) separating from the aromatic hydrocarbon mixture an isobutane-containing gaseous fraction and an aromatic liquid fraction boiling in the gasoline range;

(d) converting the isobutane-containing gaseous fraction by alkylation into a product from which a fraction boiling in the gasoline range is separated; and (e) mixing the two fractions boiling in the gasoline range obtained according to (c) and (d).

* * * * *